(12) United States Patent
Cao et al.

(10) Patent No.: US 10,789,498 B2
(45) Date of Patent: Sep. 29, 2020

(54) SYSTEMS AND METHODS FOR PATIENT POSITIONING

(71) Applicant: SHANGHAI UNITED IMAGING HEALTHCARE CO., LTD., Shanghai (CN)

(72) Inventors: Jianhui Cao, Shanghai (CN); Lei Zhang, Shanghai (CN); Yaguang Fu, Shanghai (CN); Suming Wang, Shanghai (CN); Longzi Yang, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 127 days.

(21) Appl. No.: 16/006,797

(22) Filed: Jun. 12, 2018

(65) Prior Publication Data
US 2019/0205687 A1    Jul. 4, 2019

Related U.S. Application Data

(63) Continuation of application No. PCT/CN2017/119896, filed on Dec. 29, 2017.

(51) Int. Cl.
*G06K 9/32* (2006.01)
*A61B 5/00* (2006.01)
(Continued)

(52) U.S. Cl.
CPC .......... *G06K 9/3233* (2013.01); *A61B 5/0035* (2013.01); *A61B 5/0037* (2013.01);
(Continued)

(58) Field of Classification Search
CPC ...... G06K 9/3233; G06T 7/74; A61B 5/0037; A61B 5/0046; A61B 5/0077; A61B 5/015;
(Continued)

(56) References Cited

U.S. PATENT DOCUMENTS

| 2004/0081341 A1 | 4/2004 | Cherek et al. |
| 2006/0233430 A1 | 10/2006 | Kimura |

(Continued)

FOREIGN PATENT DOCUMENTS

| CN | 102997866 A | 3/2013 |
| CN | 204863247 U | 12/2015 |

(Continued)

OTHER PUBLICATIONS

International Search Report in PCT/CN2017/119896 dated Sep. 20, 2018, 4 pages.

(Continued)

*Primary Examiner* — Leon Flores
(74) *Attorney, Agent, or Firm* — Metis IP LLC

(57) ABSTRACT

The present disclosure relates to systems and methods for positioning a subject. The method may include generating a first image of the subject disposed on a scanning board of an imaging device. The first image may include position information of the subject. The method may further include generating a second image of the subject which includes information associated with one or more organs of the subjects. Additionally, the method may include determining the position of a ROI based on the first image and the second image. The method may further include operating the imaging device to scan a target portion of the subject.

20 Claims, 13 Drawing Sheets

(51) Int. Cl.
| | |
|---|---|
| *A61B 6/00* | (2006.01) |
| *A61B 6/03* | (2006.01) |
| *A61B 6/04* | (2006.01) |
| *A61B 5/103* | (2006.01) |
| *G06T 7/73* | (2017.01) |
| *A61B 5/01* | (2006.01) |
| *A61B 5/107* | (2006.01) |

(52) U.S. Cl.
CPC .......... *A61B 5/0046* (2013.01); *A61B 5/0077* (2013.01); *A61B 5/015* (2013.01); *A61B 5/1036* (2013.01); *A61B 5/1077* (2013.01); *A61B 6/03* (2013.01); *A61B 6/032* (2013.01); *A61B 6/0407* (2013.01); *A61B 6/469* (2013.01); *G06T 7/74* (2017.01); *A61B 5/6888* (2013.01); *A61B 5/6889* (2013.01); *A61B 5/6891* (2013.01); *A61B 5/6892* (2013.01); *A61B 6/0492* (2013.01); *A61B 6/4417* (2013.01); *A61B 6/467* (2013.01); *G06K 2209/051* (2013.01); *G06T 2207/10072* (2013.01); *G06T 2207/20221* (2013.01); *G06T 2207/30204* (2013.01)

(58) Field of Classification Search
CPC ....... A61B 5/1036; A61B 5/1077; A61B 6/03; A61B 6/032; A61B 6/0407; A61B 6/469
See application file for complete search history.

(56) References Cited

U.S. PATENT DOCUMENTS

| | | | |
|---|---|---|---|
| 2013/0083894 | A1 | 4/2013 | Niebler et al. |
| 2014/0029812 | A1 | 1/2014 | Kriston et al. |
| 2014/0093134 | A1 | 4/2014 | Park et al. |
| 2017/0086758 | A1* | 3/2017 | McCarthy ................ A61B 6/10 |
| 2017/0100089 | A1 | 4/2017 | Chang et al. |
| 2017/0112416 | A1 | 4/2017 | Hao et al. |
| 2017/0143304 | A1 | 5/2017 | Malik et al. |
| 2017/0181809 | A1 | 6/2017 | Panescu et al. |
| 2017/0188011 | A1 | 6/2017 | Panescu et al. |

FOREIGN PATENT DOCUMENTS

| | | |
|---|---|---|
| CN | 205658920 U | 10/2016 |
| CN | 205849464 U | 1/2017 |
| CN | 107358607 A | 11/2017 |
| WO | 2006109308 A1 | 10/2006 |

OTHER PUBLICATIONS

Written Opinion in PCT/CN2017/119896 dated Sep. 20, 2018, 4 pages.
International Search Report in PCT/CN2017/120280 dated Sep. 6, 2018, 4 pages.
Written Opinion in PCT/CN2017/120280 dated Sep. 6, 2018, 4 pages.

* cited by examiner

1000

| Generating an image of a patient disposed on a scanning board of an imaging device, the image including position information of a reference object with respect to the imaging device and information associated with one or more organs of the patient | 1010 |

| Determining, based on the position information of the reference object, a position of a ROI with respect to the imaging device, the ROI including at least one of the one or more organs of the patient | 1020 |

FIG. 10

SYSTEMS AND METHODS FOR PATIENT POSITIONING

CROSS-REFERENCE TO RELATED APPLICATION

This application is a Continuation of International Application No. PCT/CN/2017/119896, filed on Dec. 29, 2017, the entire content of which is hereby incorporated by reference.

TECHNICAL FIELD

The present disclosure generally relates to patient positioning, and more specifically, to methods and systems for determining the position of a patient.

BACKGROUND

Medical imaging system has been widely used in clinical examinations and medical diagnosis in recent years. When using an imaging device to perform a scan, an operator (e.g., a doctor, a technician) needs to determine the position of a scanning area of a patient with respect to the imaging device. The scanning area of the patient may be determined manually by the operator with the help of a pre-scanning on the patient, which may take extra time of the operator. Further, a pre-scanning on the patient also causes extra and unnecessary radiation to the patient. Therefore, it is desirable to provide systems and methods for positioning the patient for medical imaging by the imaging device in order to save the time of the operator and reduce the extra and unnecessary radiation on the patient due to pre-scanning.

SUMMARY

According to an aspect of the present disclosure, a system may include a computer-readable storage medium storing executable instructions, and at least one processor in communication with the computer-readable storage medium. When executing the executable instructions, the at least one processor may cause the system to generate a first image of a subject disposed on a scanning board of an imaging device. The first image may include position information of the subject. The at least one processor may also cause the system to generate a second image of the subject. The second image may include information associated with one or more organs of the subject. The at least one processor may further cause the system to determine, based on the first image and the second image, a position of a region of interest (ROI) with respect to the imaging device. The ROI may include at least one of the one or more organs of the subject. The at least one processor may further cause the system to operate the imaging device to scan a target portion of the subject including the ROI of the subject.

In some embodiments, the at least one processor may cause the system to receive, from a plurality of pressure sensors disposed on the scanning board, a plurality of measurements associated with pressure generated by the subject. The at least one processor may also cause the system to generate a body contour of the subject based on the plurality of measurements associated with pressure generated by the subject. The at least one processor may further cause the system to generate the first image of the subject based on the body contour of the subject.

In some embodiments, the plurality of measurements may indicate a plurality of pressure values obtained by the plurality of pressure sensors, respectively.

In some embodiments, the at least one processor may cause the system to receive information associated with thermal distribution of the subject. The at least one processor may also cause the system to generate the second image of the subject using thermal tomography based on the thermal distribution.

In some embodiments, the at least one processor may cause the system to acquire physiological data related to the subject. The at least one processor may also cause the system to generate the second image of the subject based on the physiological data and anatomical information associated with organs of the subject.

In some embodiments, the at least one processor may cause the system to generate a third image of the subject by combining the first image and the second image. The at least one processor may also cause the system to determine, based on the third image of the subject, the position of the ROI.

In some embodiments, the at least one processor may cause the system to identify a first point of interest (POI) in the first image of the subject. The at least one processor may also cause the system to identify a second POI in the second image of the subject. The second POI and the first POI may correspond to a same physical location. The at least one processor may further cause the system to combine, based on the first POI and the second POI, the first image and the second image.

In some embodiments, the at least one processor may cause the system to identify a third POI in the first image of the subject. The at least one processor may also cause the system to identify a fourth POI in the second image of the subject. The third POI and the fourth POI may correspond to a same physical location. The at least one processor may further cause the system to determine, based on the third POI and the fourth POI, the position of the ROI.

In some embodiments, the at least one processor may cause the system to determine at least one boundary line to delimit the target portion. The at least one processor may also cause the system to operate the imaging device to scan the subject according to the at least one boundary line.

According to another aspect of the present disclosure, a computer-implemented method may include one or more of the following operations performed by at least one processor. The method may include generating a first image of a subject disposed on a scanning board of the imaging device. The first image may include position information of the subject with respect to the imaging device. The method may also include generating a second image of the subject. The second image may include information associated with one or more organs of the subject. The method may also include determining, based on the first image and the second image, a position of a region of interest (ROI) with respect to the imaging device. The ROI may include at least one of the one or more organs of the subject. The method may further include operating the imaging device to scan a target portion of the subject including the ROI of the subject.

According to yet another aspect of the present disclosure, a computer-implemented method may include one or more of the following operations performed by at least one processor. The method may include generating an image of the subject disposed on a scanning board of the imaging device. The image may include position information of a reference object located outside the subject with respect to the imaging device and information associated with one or more organs of the subject. The method may also include determining, based on the reference object located outside the subject, a position of a region of interest (ROI) with respect to the imaging device. The ROI may include at least one of the one or more organs of the subject. The method may further include operating the imaging device to scan a target portion of the subject including the ROI of the subject.

In some embodiments, the reference object may be a marker installed on the scanning board.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 10 is a flowchart illustrating an exemplary process for determining the position of a ROI with respect to an imaging device according to some embodiments of the present disclosure;

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by other expression if they achieve the same purpose.

Figure 2:
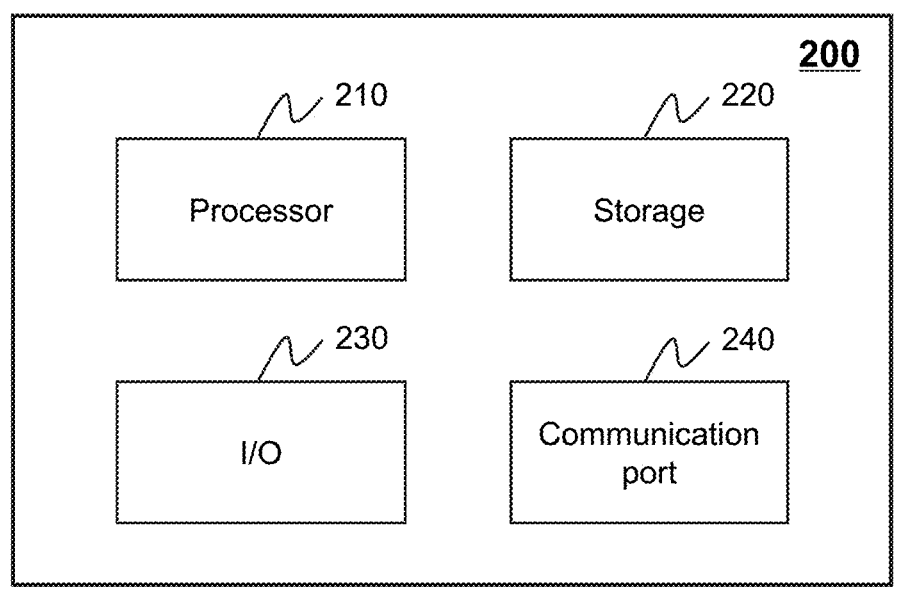
FIG. 2 is a schematic diagram illustrating exemplary hardware and/or software components of an exemplary computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and components for positioning a patient in an imaging device. In some embodiments, the imaging device may be used in a single-modality imaging system, such as a computed tomography (CT) system, an emission computed tomography (ECT) system, an ultrasonography system, an X-ray photography system, a positron emission tomography (PET) system, a radiation theraphy (RT) system, or the like, or any combination thereof. In some embodiments, the imaging device may be used in a multi-modality imaging system, such as, a computed tomography-magnetic resonance imaging (CT-MRI) system, a positron emission tomography-magnetic resonance imaging (PET-MRI) system, a single photon emission computed tomography-computed tomography (SPECT-CT) system, a digital subtraction angiography-computed tomography (DSA-CT) system, etc. It should be noted that the imaging system 100 described below is merely provided for illustration purposes, and not intended to limit the scope of the present disclosure.

To address the deficiencies of the conventional techniques, the present disclosure provides mechanisms (which can include methods, systems, computer-readable medium, etc.) for positioning a patient for medical examination by an imaging device. For example, the methods and/or systems according to the present disclosure may determine the position of the patient or a region of interest (ROI) thereof based on at least one image related to the subject. In some embodiments, the at least one image may include an image of body contour having position information of the patient with respect to the imaging device and a structure image indicating the position of the ROI inside the patient. In some embodiments, the at least one image may be an image that has position information of the ROI of the patient. After the position of the ROI is determined, the method and/or system according to the present disclosure may operate the imaging device to scan a target portion of the subject including the ROI of the subject.

The following description is provided to help better understanding patient positioning methods and/or systems. This is not intended to limit the scope the present disclosure. For persons having ordinary skills in the art, a certain amount of variations, changes, and/or modifications may be deducted under the guidance of the present disclosure. Those variations, changes, and/or modifications do not depart from the scope of the present disclosure.

Figure 1:
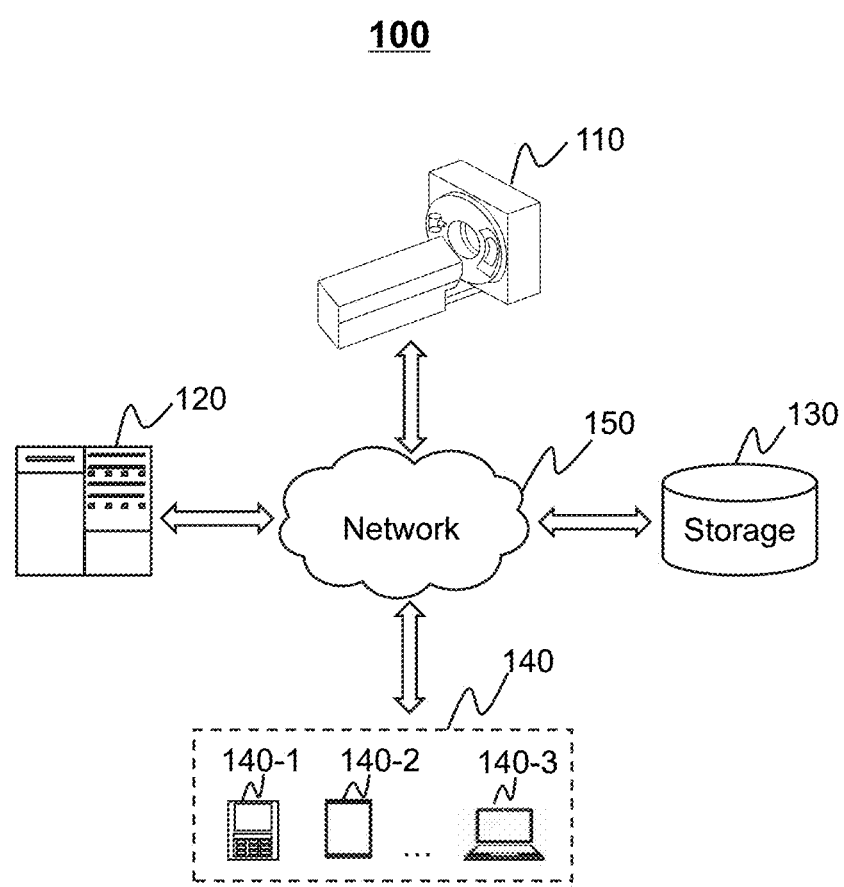
FIG. 1 is a schematic diagram illustrating an exemplary imaging system according to some embodiments of the present disclosure.

FIG. 1 is schematic diagrams illustrating an exemplary imaging system 100 according to some embodiments of the present disclosure. As shown, the imaging system 100 may include a imaging device 110, a processing engine 120, a storage 130, one or more terminals 140, and a network 150. In some embodiments, the imaging device 110, the processing engine 120, the storage 130, and/or the terminal(s) 140 may be connected to and/or communicate with each other via a wireless connection (e.g., the network 150), a wired connection, or a combination thereof. The connection between the components of the imaging system 100 may be variable. Merely by way of example, the imaging device 110 may be connected to the processing engine 120 through the network 150, as illustrated in FIG. 1. As another example, the imaging device 110 may be connected to the processing engine 120 directly. As a further example, the storage 130 may be connected to the processing engine 120 through the network 150, as illustrated in FIG. 1, or connected to the processing engine 120 directly. As still a further example, a terminal 140 may be connected to the processing engine 120 through the network 150, as illustrated in FIG. 1, or connected to the processing engine 120 directly.

The imaging device 110 may generate or provide image data via scanning a subject (e.g., a patient) disposed on a scanning board of the imaging device 110. In some embodiments, the imaging device 110 may include a single-modality scanner and/or multi-modality scanner. The single-modality scanner may include, for example, a computed tomography (CT) scanner. The multi-modality scanner may include a single photon emission computed tomography-computed tomography (SPECT-CT) scanner, a positron emission tomography-computed tomography (PET-CT) scanner, a computed tomography-ultra-sonic (CT-US) scanner, a digital subtraction angiography-computed tomography (DSA-CT) scanner, or the like, or a combination thereof. In some embodiments, the image data may include projection data, images relating to the subject, etc. The projection data may be raw data generated by the imaging device 110 by scanning the subject, or data generated by a forward projection on an image relating to the subject. In some embodiments, the subject may include a body, a substance, an object, or the like, or a combination thereof. In some embodiments, the subject may include a specific portion of a body, such as a head, a thorax, an abdomen, or the like, or a combination thereof. In some embodiments, the subject may include a specific organ or region of interest, such as an esophagus, a trachea, a bronchus, a stomach, a gallbladder, a small intestine, a colon, a bladder, a ureter, a uterus, a fallopian tube, etc.

In some embodiments, the imaging device 110 may include a tube, a detector, etc. The tube may generate and/or emit radiation beams travelling toward the subject according to one or more scanning parameters. The radiation may include a particle ray, a photon ray, or the like, or a combination thereof. In some embodiments, the radiation may include a plurality of radiation particles (e.g., neutrons, protons, electron, p-mesons, heavy ions), a plurality of radiation photons (e.g., X-ray, a y-ray, ultraviolet, laser), or the like, or a combination thereof. Exemplary scanning parameters may include a tube current/voltage, an integration time of a detector, a focus size of a tube, a response of a detector, a response of a tube, a width of a collimation, a slice thickness, a slice gap, a field of view (FOV), etc.

The detector in the imaging device 110 may detect radiation beams. In some embodiments, the detector of the imaging device 110 may include one or more detector units that may detect a distribution of the radiation beams emitted from the tube or scattered by the subject. In some embodiments, the detector of the imaging device 110 may be connected to a data conversation circuit configured to convert the distribution of the detected radiation beams into image data (e.g., projection data).

In some embodiments, the imaging device 110 may be integrated with one or more other devices that may facilitate the scanning of the subject, such as, an image-recording device. The image-recording device may be configured to take various types of images related to the subject. For example, the image-recording device may be a two-dimensional (2D) camera that takes pictures of the exterior or body contour of the subject. As another example, the image-recording device may be a three-dimensional (3D) scanner (e.g., a laser scanner, an infrared scanner, a 3D CMOS sensor) that records the spatial representation of the subject.

The processing engine 120 may process data and/or information obtained from the imaging device 110, the storage 130, the terminal(s) 140, or other components of the imaging system 100. For example, the processing engine 120 may reconstruct an image based on projection data generated by the imaging device 110. As another example, the processing engine 120 may determine the position of a target region (e.g., a region in a patient) to be scanned by the imaging device 110. In some embodiments, the processing engine 120 may be a single server or a server group. The server group may be centralized or distributed. In some embodiments, the processing engine 120 may be local to or remote from the imaging system 100. For example, the processing engine 120 may access information and/or data from the imaging device 110, the storage 130, and/or the terminal(s) 140 via the network 150. As another example, the processing engine 120 may be directly connected to the imaging device 110, the terminal(s) 140, and/or the storage 130 to access information and/or data. In some embodiments, the processing engine 120 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing engine 120 may be implemented by a computing device 200 having one or more components as described in connection with FIG. 2.

The storage 130 may store data, instructions, and/or any other information. In some embodiments, the storage 130 may store data obtained from the processing engine 120, the terminal(s) 140, and/or the interaction device 150. In some embodiments, the storage 130 may store data and/or instructions that the processing engine 120 may execute or use to perform exemplary methods described in the present disclosure. In some embodiments, the storage 130 may include a mass storage, a removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 130 may be implemented on a cloud platform as described elsewhere in the disclosure.

In some embodiments, the storage 130 may be connected to the network 150 to communicate with one or more other components of the imaging system 100 (e.g., the processing engine 120, the terminal(s) 140). One or more components of the imaging system 100 may access the data or instructions stored in the storage 130 via the network 150. In some embodiments, the storage 130 may be part of the processing engine 120.

The terminal(s) 140 may be connected to and/or communicate with the imaging device 110, the processing engine 120, and/or the storage 130. For example, the terminal(s) 140 may obtain a processed image from the processing engine 120. As another example, the terminal(s) 140 may obtain image data acquired via the imaging device 110 and transmit the image data to the processing engine 120 to be processed. In some embodiments, the terminal(s) 140 may include a mobile device 140-1, a tablet computer 140-2, a laptop computer 140-3, or the like, or any combination thereof. For example, the mobile device 140-1 may include a mobile phone, a personal digital assistance (PDA), a gaming device, a navigation device, a point of sale (POS) device, a laptop, a tablet computer, a desktop, or the like, or any combination thereof. In some embodiments, the terminal(s) 140 may include an input device, an output device, etc. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to the processing engine 120 via, for example, a bus, for further processing. Other types of the input device may include a cursor control device, such as a mouse, a trackball, or cursor direction keys, etc. The output device may include a display, a speaker, a printer, or the like, or a combination thereof. In some embodiments, the terminal(s) 140 may be part of the processing engine 120.

The network 150 may include any suitable network that can facilitate exchange of information and/or data for the imaging system 100. In some embodiments, one or more components of the imaging system 100 (e.g., the imaging device 110, the processing engine 120, the storage 130, the terminal(s) 140) may communicate information and/or data with one or more other components of the imaging system 100 via the network 150. For example, the processing engine 120 may obtain image data from the imaging device 110 via the network 150. As another example, the processing engine 120 may obtain user instruction(s) from the terminal(s) 140 via the network 150. The network 150 may be or include a public network (e.g., the Internet), a private network (e.g., a local area network (LAN)), a wired network, a wireless network (e.g., an 802.11 network, a Wi-Fi network), a frame relay network, a virtual private network (VPN), a satellite network, a telephone network, routers, hubs, switches, server computers, and/or any combination thereof. For example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the imaging system 100 may be connected to the network 150 to exchange data and/or information.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the storage 130 may be a data storage including cloud computing platforms, such as, public cloud, private cloud, community, and hybrid clouds, etc. However, those variations and modifications do not depart the scope of the present disclosure.

FIG. 2 is a schematic diagram illustrating exemplary hardware and/or software components of an exemplary computing device 200 on which the processing engine 120 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (e.g., program code) and perform functions of the processing engine 120 in accordance with techniques described herein. The computer instructions may include, for example, routines, programs, objects, components, data structures, procedures, modules, and functions, which perform particular functions described herein. For example, the processor 210 may process image data obtained from the imaging device 110, the terminals 140, the storage 130, and/or any other component of the imaging system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method operations that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operation s A and B).

The storage 220 may store data/information obtained from the imaging device 110, the terminals 140, the storage 130, and/or any other component of the imaging system 100. In some embodiments, the storage 220 may include a mass storage, a removable storage, a volatile read-and-write memory, a read-only memory (ROM), or the like, or any combination thereof. For example, the mass storage may include a magnetic disk, an optical disk, a solid-state drives, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing engine 120 for determining the position of a target region of a subject (e.g., a target portion of a patient).

The I/O 230 may input and/or output signals, data, information, etc. In some embodiments, the I/O 230 may enable a user interaction with the processing engine 120. In some embodiments, the I/O 230 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 240 may be connected to a network (e.g., the network 150) to facilitate data communications. The communication port 240 may establish connections between the processing engine 120 and the imaging device 110, the terminals 140, and/or the storage 130. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
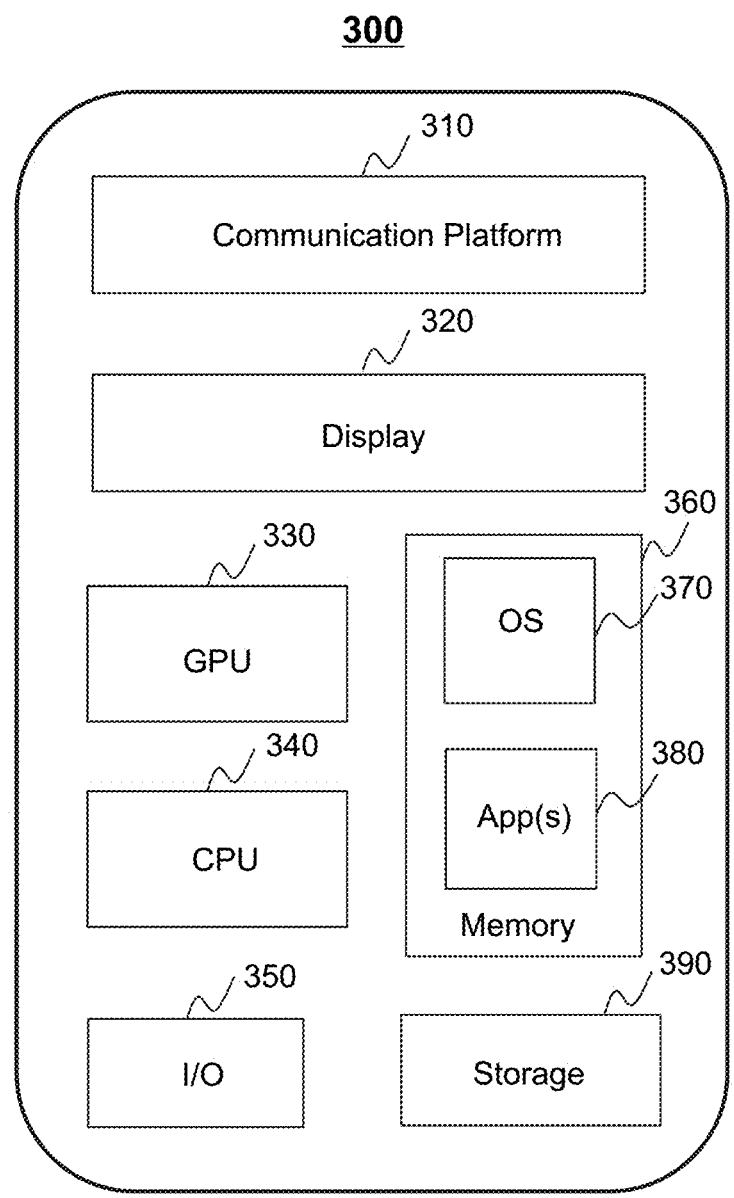
FIG. 3 is a schematic diagram illustrating exemplary hardware and/or software components of an exemplary mobile device according to some embodiments of the present disclosure.

FIG. 3 is a schematic diagram illustrating exemplary hardware and/or software components of an exemplary mobile device 300 on which the terminals 140 may be implemented according to some embodiments of the present disclosure. As illustrated in FIG. 3, the mobile device 300 may include a communication platform 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™) and one or more applications 380 may be loaded into the memory 360 from the storage 390 in order to be executed by the CPU 340. The applications 380 may include a browser or any other suitable mobile apps for receiving and rendering information relating to image processing or other information from the processing engine 120. User interactions with the information stream may be achieved via the I/O 350 and provided to the processing engine 120 and/or other components of the imaging system 100 via the network 150.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
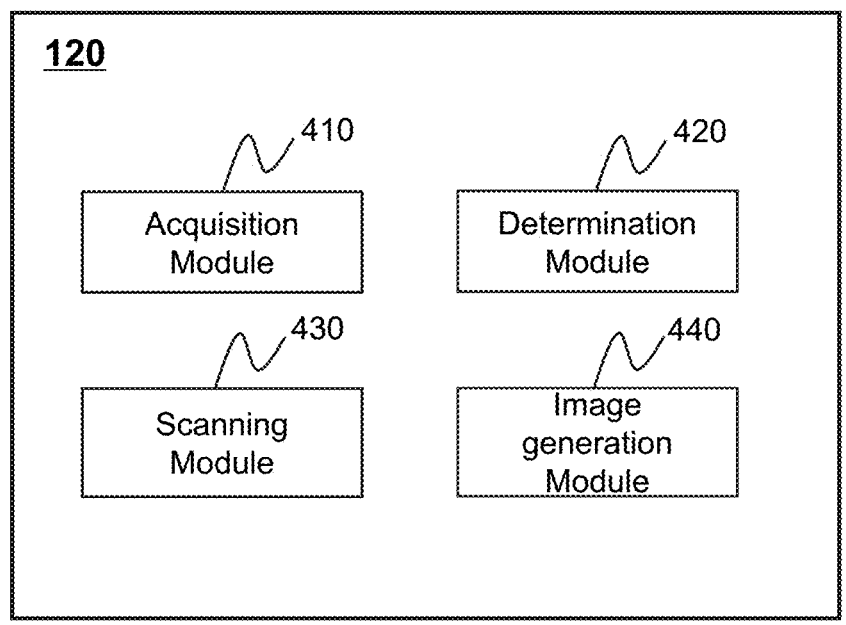
FIG. 4 is a block diagram illustrating an exemplary processing engine according to some embodiments of the present disclosure.

FIG. 4 is a block diagram illustrating an exemplary processing engine 120 according to some embodiments of the present disclosure. The processing engine 120 may include an acquisition module 410, a determination module 420, a scanning module 430, and an image generation module 440. The processing engine 120 may be implemented on various components (e.g., the processor 210 of the computing device 200 as illustrated in FIG. 2). For example, at least a portion of the processing engine 120 may be implemented on a computing device as illustrated in FIG. 2 or a mobile device as illustrated in FIG. 3.

The acquisition module 410 may acquire various data or information from other components of the imaging system 100. For example, the acquisition module 410 may acquire physiological data related to a patient to facilitate the subsequent scanning on the patient. As another example, the acquisition module 410 may acquire image data related to a patient from the imaging device 110 and transmit the image data to the image generation module for generating an image related to the patient.

The determination module 420 may determine information related to a target region to be scanned. For example, the determination module 420 may identify the position of a ROI (region of interest) and a target region including the ROI.

The scanning module 430 may generate instructions to operate an imaging device (e.g., the imaging device 110). For example, the scanning module 430 may generate instructions to adjust the position of the scanning board of the imaging device or adjust the position of the tube that emits radiation beams. As another example, the scanning module 430 may generate instruction to guide the scanning on a patient.

The image generation module 440 may generate at least one type of image related to a patient. The at least one type of image related to a patient may provide information that helps scanning the patient, e.g., in positioning the patient with respect to the imaging device 110.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, the processing engine 120 may include a storage module configured to store data or information before or during the scanning process.

Figure 5:
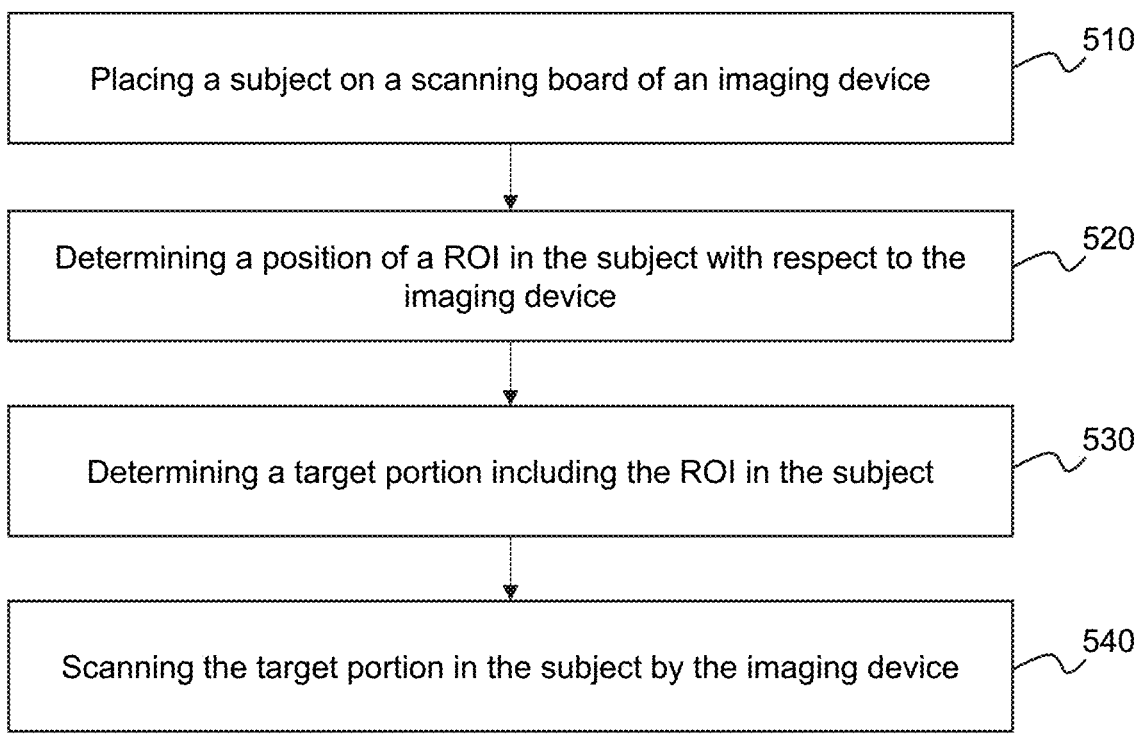
FIG. 5 is a flowchart illustrating an exemplary process for scanning a subject by an imaging device according to some embodiments of the present disclosure.

FIG. 5 is a flowchart illustrating an exemplary process 500 for scanning a subject by an imaging device according to some embodiments of the present disclosure. In some embodiments, one or more operations of process 500 illustrated in FIG. 5 for scanning a subject may be implemented in the imaging system 100 illustrated in FIG. 1. For example, at least a part of the process 500 illustrated in FIG. 5 may be stored in the storage 130 in the form of instructions, and invoked and/or executed by the processing engine 120 (e.g., the processor 210 of the computing device 200 as illustrated in FIG. 2, the GPU 330 or CPU 340 of the mobile device 300 as illustrated in FIG. 3).

In 510, a subject may be placed on a scanning board of an imaging device (e.g., the imaging device 110). The subject may relate to an organic or inorganic mass that has a chemical, biochemical, biological, physiological, biophysical and/or physical activity or function. In some embodiments, the subject may include cells, tissues, organs or whole body of a human or animal. For illustration purpose, a patient is taken as an example of the subject. The patient may lie on the scanning board and the entire body of the patient may occupy a specific area on the scanning board. In some embodiments, the scanning board may be configured with various detecting units to obtain information related to the patient. Exemplary information may include the body contour of the patient, a plurality of pressures generated by the body of the patient, the pressure distribution on the specific area of the scanning board, the height of the patient, the temperature of the patient, or the like, or a combination thereof. Exemplary detecting units may include pressure sensors, temperature sensors, or the like, or a combination thereof. Merely by way of example, a plurality of pressure sensors may be arranged on the scanning board to detect a plurality of pressures generated by the body of the patient. More descriptions regarding the generation of the image of body contour may be found elsewhere in the disclosure (e.g., in connection with FIG. 7 and the description thereof).

In 520, the determination module 420 may determine a position of a ROI in the subject. In some embodiments, the determination module 420 may determine the position of the ROI with respect to the imaging device (e.g., the position of the ROI in the subject with respect to the scanning board of the imaging device). Alternatively, the determination module 420 may determine the position of the ROI with respect to a specific location that is recognizable to, for example, the scanning module 430. In the following descriptions, for illustration purposes, the position of the ROI with respect to the image device may be illustrated as an example.

The ROI may be the entire body of the subject, a portion of the subject or one or more organs of the subject depending on the diagnostic needs. For example, when the doctor's order is to image the patient's lungs, the ROI may be the chest area that includes the lungs and heart. As another example, when the doctor's order is to image the womb, the ROI may include both ovaries in addition to the womb. The information of the ROI may be processed by the processing engine 120 of the imaging system 100 and the ROI may be illustrated on a graphic user interface (GUI). As such, an operator of the imaging device (e.g., the imaging device 110) may be capable of positioning the ROI and moving the scanning board with the subject to a target position for scanning.

In some embodiments, the position of the ROI in the subject with respect to the imaging device may be determined according to the position information of the subject with respect to the imaging device and the relative position of the ROI inside the subject. The position information of the subject with respect to the imaging device may be determined according to an image of body contour associated with the subject where the spatial correlation between the subject and the scanning board is determined. Specifically, the image of body contour associated with the subject may present the body contour of the subject on the scanning board. The relative position of the ROI inside the subject may be determined according to a structure image associated with the subject where the spatial correlation between the ROI and the subject is presented. As used herein, the structure image may refer to an image that presents a perspective view of a subject. For example, a structure image of a patient may present one or more organs of the patient. More descriptions regarding the determination of the position of the ROI may be found elsewhere in the present disclosure (e.g., in connection with FIG. 6 and the description thereof).

In some embodiments, the position of the ROI in the subject with respect to the imaging device may be determined according to the spatial correlation between the ROI and a reference object located outside the subject (e.g., a marker installed on the scanning board). More descriptions regarding the determination of the position of the ROI according to a reference object may be found elsewhere in the present disclosure (e.g., in connection with FIG. 10 and the description thereof).

In 530, the determination module 420 may determine a target portion including the ROI in the subject. In some embodiments, the determination module 420 may determine at least a boundary line to delimit a target portion. The target portion may be large enough to cover the ROI. For example, if the ROI corresponds to the lung region of a patient, the determination module 420 may designate the whole chest as the target portion such that the subsequent scanning may cover the whole area of the ROI.

In some embodiments, the target portion may be determined manually by an operator or automatically by the determination module 420. For example, an operator may manually set the target portion on an image of the subject displayed on the GUI. The operator may draw an area on the image of the subject displayed on the GUI to set the target portion. Alternatively, the operator may select one or more reference points on the image of the subject displayed on the GUI to set the target portion. As another example, the determination module 420 may automatically set a target portion based on the position of the ROI with respect to the imaging device and information related to a scanning protocol of the subject. The size and shape of the target portion may be pre-configured with respect to one or more particular organs in the imaging system 100. When the ROI includes one or more particular organs, the determination module 420 may generate a target portion based on the system pre-configuration. The scanning protocol may indicate the relationship between a ROI and a corresponding target portion (e.g., the sizes of the ROI and the corresponding target portion). In some embodiments, the information related to the scanning protocol of the patient may be stored in one or more storage devices in the imaging system 100 (e.g., the storage device 160).

In 540, the imaging device may scan the target portion of the subject. In some embodiments, the scanning module 430 may generate instructions to operate the imaging device to scan the target portion.

For example, the scanning module 430 may send instructions to operate the imaging device to adjust the position of the scanning board to a suitable location such that only the target portion of the subject is scanned. The instructions may involve various parameters related to the movement of the scanning board. Exemplary parameters related to the movement of the scanning board may include the distance of movement, the direction of movement, the speed of movement, or the like, or a combination thereof.

As another example, the scanning module 430 may send instructions to operate the imaging device to adjust the position of other components of the imaging device, e.g., the tube that emits the radiation beams, or other mechanical parts connected to the scanning board.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. In some embodiments, one or more operations may be added or omitted. For example, the operation 540 may be divided into multiple operations which include determining parameters related to moving one or more components of the imaging device. As another example, an operation to acquire information related to the scanning protocol of the subject may be added before the operation 530.

Figure 6:
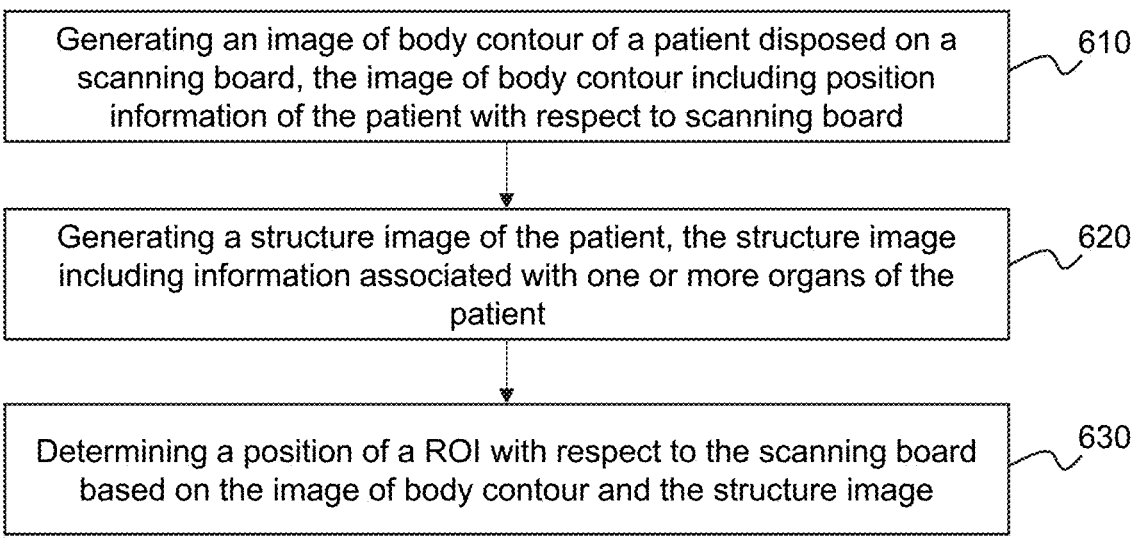
FIG. 6 is flowchart illustrating an exemplary process 600 for determining the position of a ROI with respect to an imaging device according to some embodiments of the present disclosure.

FIG. 6 is a flowchart illustrating an exemplary process 600 for determining the position of a ROI with respect to an imaging device according to some embodiments of the present disclosure. In some embodiments, the operation 520 as illustrated in FIG. 5 may be performed according to process 600. In some embodiments, one or more operations of process 600 illustrated in FIG. 6 may be implemented in the imaging system 100 illustrated in FIG. 1. For example, the process 600 may be stored in the storage 130 in the form of instructions, and invoked and/or executed by the processing engine 120 (e.g., the processor 210 of the computing device 200 as illustrated in FIG. 2, the GPU 330 or CPU 340 of the mobile device 300 as illustrated in FIG. 3).

In 610, the image generation module 440 may generate an image of body contour of a patient disposed on a scanning board. The image of body contour of the patient may include position information of the patient with respect to the scanning board.

In some embodiments, the image of body contour of the patient may be generated according to information collected by a plurality of pressure sensors arranged on the scanning board. For example, the plurality of pressure sensors may measure the pressure values generated by the patient on different parts of the scanning board and obtain a pressure distribution on the scanning board. The processing engine 120 may further transform the pressure measurements into voltage signals, from which the image of body contour of the patient is generated. The image of body contour of the patient on the scanning board may further illustrate the spatial correlation between the patient and the scanning board. More descriptions regarding the generation of the image based on the pressure measurements from the pressure sensors may be found elsewhere in the present disclosure (e.g., in connection with FIG. 7 and the description thereof).

Alternatively, in some embodiments, the image of body contour may be generated by at least a camera. The at least one camera may be arranged to take photos of the patient on the scanning board. For example, the at least one camera may be mounted on the gantry of an imaging device to record the position of the patient with respect to the scanning board. In some embodiments, a camera may be mounted on the ceiling of the gantry to record the front of the patient on the scanning board. In some embodiments, a camera may be mounted on the side of the gantry to record the side view of the patient on the scanning board. In some embodiments, a plurality of cameras may be mounted on different positions of the gantry to record a perspective view of the patient on the scanning board.

In 620, the image generation module 440 may generate a structure image of the patient including information associated with one or more organs of the patient. Exemplary information associated with one or more organs of the patient may include the relative positions of the one or more organs inside the patient, the shapes of the one or more organs, the sizes of the one or more organs, or the like, or a combination thereof.

In some embodiments, the structure image of the subject may be generated by a thermal imaging device. For example, the thermal imaging device may be a thermal imaging camera which can detect the thermal radiations from the patient. The thermal imaging device may determine the heat distribution on the surface of the patient based on the thermal radiations. The thermal imaging device may further employ a thermoelectric analogy technique to determine one or more heat sources (e.g., the one or more organs) of the patient based on the heat distribution on the surface of the patient. The thermal imaging device may obtain information related to the one or more heat sources of the patient including but not limited to thermal radiation level associated with each of the one or more heat sources, depth of each of the one or more heat sources beneath the surface of the patient, position of each of the one or more heat sources beneath the surface of the patient, shape of each of the one or more heat sources beneath the surface of the patient, variation of each of the one or more heat sources beneath the surface of the patient, etc. Furthermore, the positions/shapes of the one or more heat sources (e.g., the one or more organs in the patient) may be illustrated in the structure image after one or more imaging processing operations, e.g., image filtering, image enhancing, image sharpening, or the like, or any combination thereof.

In some embodiments, the thermal imaging device may be mounted on the gantry to acquire the thermal distribution information of the patient. The thermal imaging device may be retracted in the gantry or a container mounted on the gantry when not in use, and extended from the gantry or the container when in use. For example, an extendable pole may be used to control the position of the thermal imaging device. In some embodiments, the thermal imaging device may include a plurality of sub-thermal imaging devices arranged in an arc. Additionally or alternatively, a plurality of thermal imaging devices may be mounted on the gantry to acquire information associated with the patient from different perspectives. Exemplary configuration and/or arrangement of one or more thermal imaging devices may be found in, for example, International Application entitled "SYSTEMS AND METHODS FOR DETERMINING A REGION OF INTEREST IN MEDICAL IMAGING" filed on even date of the present application, the contents of which are hereby incorporated by reference.

Figure 8:
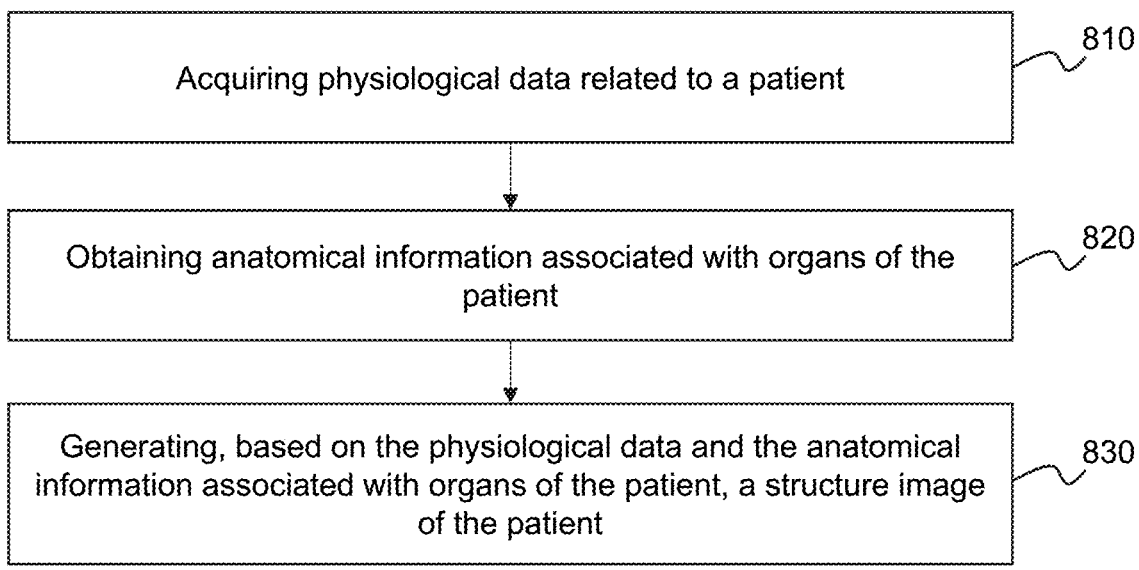
FIG. 8 is a flowchart illustrating an exemplary process for determining a structure image of a patient according to some embodiments of the present disclosure.

Alternatively, in some embodiments, the structure image may be generated by modelling the one or more organs in the patient based on the physiological data and the anatomical information associated with the organs of the patient as described in FIG. 8.

In 630, the determination module 420 may determine the position of a ROI with respect to the scanning board based on the image of body contour and the structure image. The ROI may include at least one of the one or more organs of the patient. In some embodiments, the determination module 420 may combine the image of body contour and the structure image such that the position of the ROI with respect to the scanning board may be directly presented in the combined image. Additionally or alternatively, the determination module 420 may not combine the image of body contour and the structure image. The determination module 420 may determine the position of the ROI with respect to the scanning board based on the position information of the patient with respect to the scanning board and the relative position of the ROI inside the patient. More descriptions regarding the determination of the position of the ROI may be found elsewhere in the present disclosure (e.g., in connection with FIG. 9 and FIG. 10 and the descriptions thereof).

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. In some embodiments, one or more operations may be added or omitted. For example, the operation 610 may be omitted. Instead, the position information of the patient may be determined by an operator of the imaging system 100. As another example, the operation 620 may be omitted. Instead, the information associated with one or more organs of the patient may be acquired from one or more components of the imaging system 100 (e.g., the storage 160, the storage 220, and the storage 390) or an external database. In some embodiments, operation 610 and operation 620 may be performed simultaneously.

Figure 7:
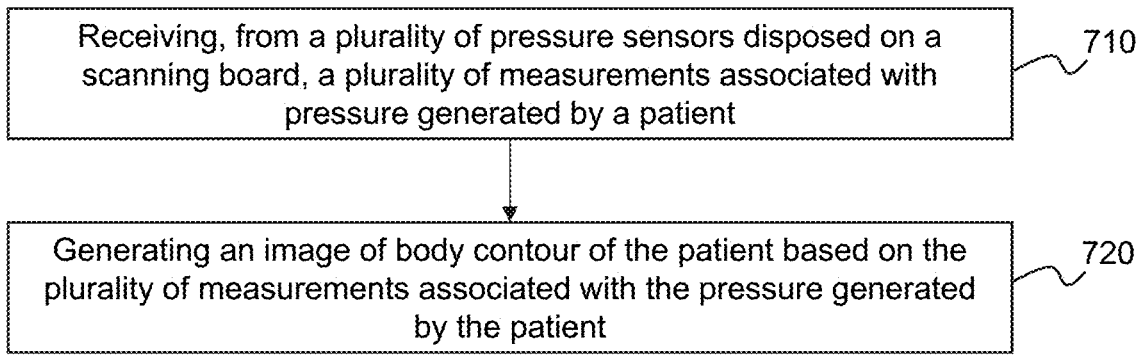
FIG. 7 is a flowchart illustrating an exemplary process for generating an image of body contour of a patient according to some embodiments of the present disclosure.

FIG. 7 is a flowchart illustrating an exemplary process 700 for generating an image of body contour of a patient according to some embodiments of the present disclosure. In some embodiments, the operation 610 as illustrated in FIG. 6 may be performed according to the process 700. In some embodiments, one or more operations of the process 700 may be implemented in the imaging system 100 illustrated in FIG. 1. For example, at least a part of the process 700 illustrated may be stored in the storage 130 in the form of instructions, and invoked and/or executed by the processing engine 120 (e.g., the processor 210 of the computing device 200 as illustrated in FIG. 2, the CPU 340 of the mobile device 300 as illustrated in FIG. 3).

Figure 13:
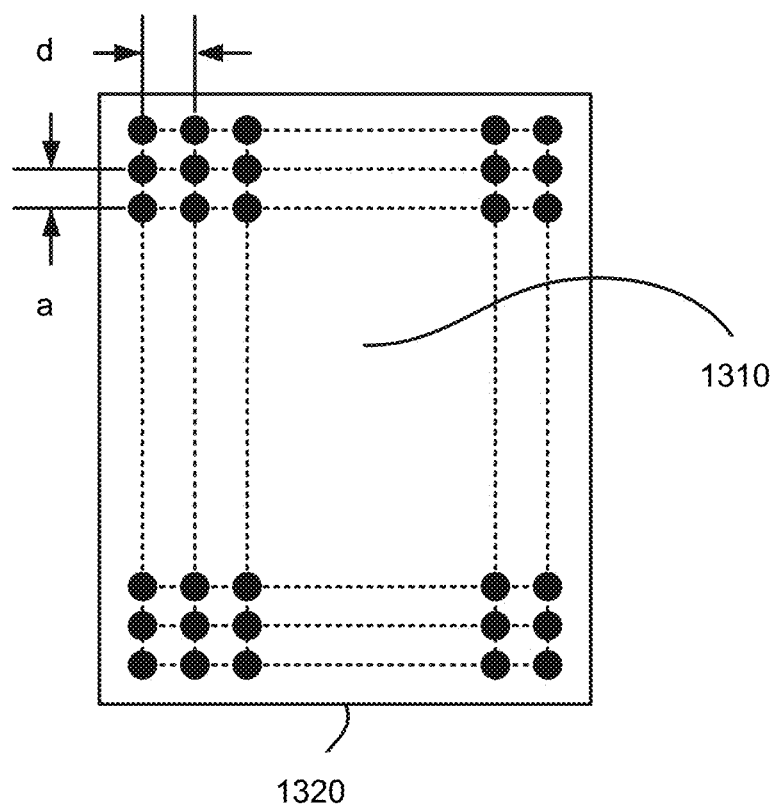
FIG. 13 is a schematic diagram illustrating a pressure sensor network arranged on a scanning board according to some embodiments of the present disclosure.

In 710, the image generation module 440 may receive a plurality of measurements from a plurality of pressure sensors disposed on a scanning board. The measurements may be associated with the pressure generated by a patient on the scanning board. In some embodiments, the plurality of pressure sensors may be arranged to form a pressure sensor network on the scanning board. For example, the pressure sensor network may be mapped into a 2D matrix as shown in FIG. 13, where a dot may represent a pressure sensor. In each row of the pressure sensor network, the pressure sensors may be evenly or unevenly distributed. In a same row or column, a pressure sensor may be spaced from its neighboring pressure sensor by a specific distance, e.g., 1 cm.

In some embodiments, the measurements may be in the form of pressure values. A larger measurement value detected by a pressure sensor may correspond to a larger pressure imposed on the pressure sensor by the patient on the scanning board. For example, when a patient lies on the scanning board, the pressure imposed by the shoulder on the scanning board may be larger than the pressure imposed by the feet on the scanning board. Thus, the pressure sensors under the shoulder of the patient may generate larger measurement values than that of the pressure sensors under the feet of the patient.

In 720, the image generation module 440 may generate an image of body contour of the patient based on the plurality of measurements associated with the pressure generated by the patient.

In some embodiments, the image of body contour of the patient may be presented in the form of a gray level image. As used herein, the gray level image may include a plurality of pixel points. Each pixel point may have a gray value that is associated with the measurement value detected by a pressure sensor. In some embodiments, a larger measurement value (e.g., a pressure value) detected by a pressure sensor may correspond to a higher gray level in the gray level image.

In some embodiments, the image of body contour of the patient may be presented in the form of a binary image. To form the binary image, the measurement values (e.g., pressure values) of the plurality of pressure sensors may be converted into binary values. For example, the measurement values which are above a threshold may be set to a first numeral (e.g., "1"), and the measurement values which are below the threshold may be set to a second numeral (e.g., "0"). The threshold may be a default value stored in a storage device (e.g., the storage device 160) or be set by an operator.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. In some embodiments, one or more operations may be added or omitted. For example, an operation of determining the information related to the patient (e.g., weight, height of the patient) may be added before the operation 720.

FIG. 8 is a flowchart illustrating an exemplary process 800 for determining a structure image of a patient according to some embodiments of the present disclosure. The operation 620 as illustrated in FIG. 6 may be performed according to the process 800. In some embodiments, one or more operations of the process 800 may be implemented in the imaging system 100 illustrated in FIG. 1. For example, the process 800 may be stored in the storage 130 in the form of instructions, and invoked and/or executed by the processing engine 120 (e.g., the processor 210 of the computing device 200 as illustrated in FIG. 2, the CPU 340 of the mobile device 300 as illustrated in FIG. 3).

In 810, the acquisition module 410 may acquire physiological data related to a patient. Exemplary physiological data related to a patient may include the electrocardiogram, the pulse wave, the blood pressure, the heart rate, the body temperature, the brain wave, the respiration, the status of muscle or skeleton, the height, the weight, or the like, or a combination thereof. In some embodiments, the physiological data may be historical data retrieved from a storage device (e.g., the storage device 160). In some embodiments, the physiological data may be measured in real time when the patient lies on the scanning board for medical examination. For example, the weight of the patient may be acquired by summing up the pressure values of all pressure sensors arranged on the scanning board. As another example, the height of the patient may be acquired based on the farthest distance along the long axis of the scanning board between two pressure sensors with pressure values detected. As used herein, the long axis of the scanning board may be the scanning direction of the patient or the direction along which the scanning board is transported.

In 820, the acquisition module 410 may obtain anatomical information associated with organs of the patient. The anatomical information associated with organs of the patient may include the position information of the organs inside the patient, the size information of the organs, the shape information of the organs, or the like, or a combination thereof. The positions information of the organs inside patient may indicate the relative spatial correlations between different organs. The size information of the organs may indicate the relative dimensions of different organs. The shape information may indicate the shapes of different organs. In some embodiments, the anatomical information may be acquired according to history data related the patient (e.g., a historical medical image of the patient). In some embodiments, the anatomical information may be acquired from a plurality of samples (e.g., images) showing the organs of different persons. For example, the size information of an organ may be in associated with the average size of same organs in the plurality of samples. Specifically, the plurality of samples may be of other persons having a similar characteristic to the patient (e.g., a similar height or weight).

In some embodiments, the anatomical information associated with organs of the patient may be stored in a storage device (e.g., the storage device 160). The acquisition module 410 may access the storage device and retrieve the anatomical information associated with organs of the patient. Additionally or alternatively, the acquisition module 410 may obtain the anatomical information associated with organs of the patient from other sources via the network 150. Other sources may include a database, a system, and/or any other source that may store anatomical information.

In 830, the image generation module 440 may generate a structure image of the patient based on the physiological data related to the patient and the anatomical information associated with organs of the patient. In some embodiments, the organs may be presented in the structure image according to the anatomical information associated with organs of the patient. In some embodiments, sizes of the organs presented in the structure image may be adjusted according to the physiological data related to the patient. For example, if the height of the patient exceeds a threshold, sizes of the organs may be scaled up to be presented in the structure image of the patient.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, the operations 810 and 820 may be performed simultaneously. As another example, the operation 820 may be performed before the operation 810.

Figure 9:
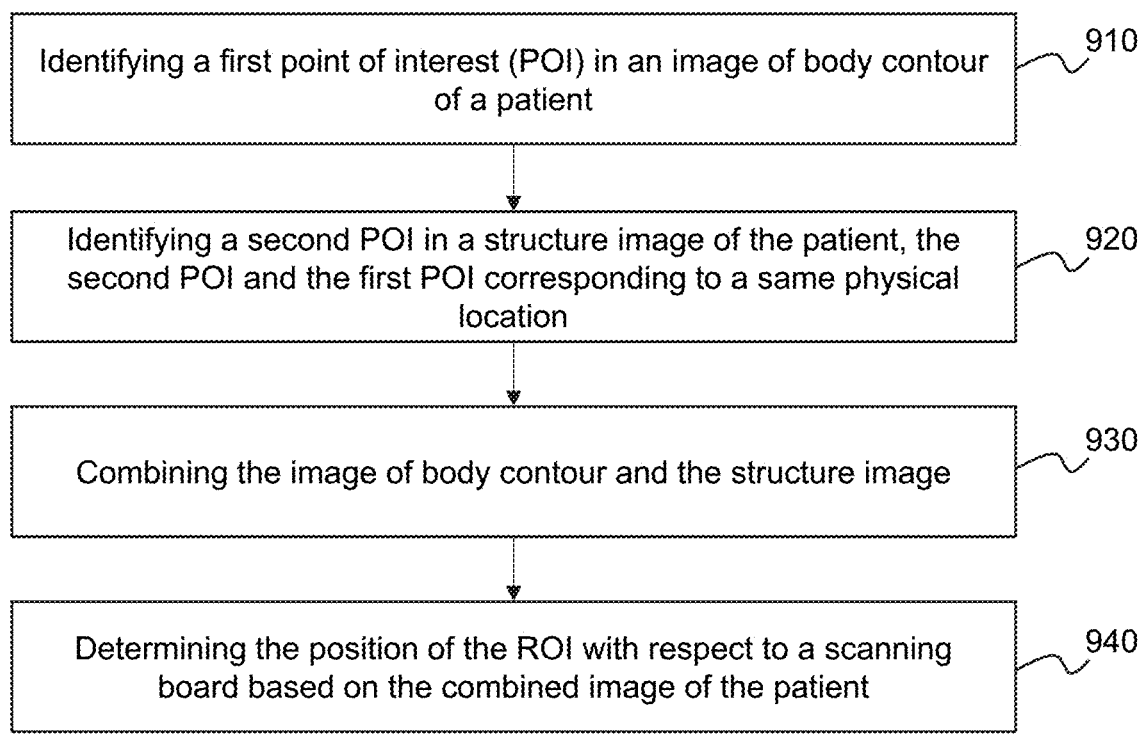
FIG. 9 is a flowchart illustrating an exemplary process for determining the position of a ROI with respect to an imaging device according to some embodiments of the present disclosure.

FIG. 9 is a flowchart illustrating an exemplary process 900 for determining the position of a ROI with respect to an imaging device according to some embodiments of the present disclosure. The operation 630 as illustrated in FIG. 6 may be performed according to the process 900. In some embodiments, one or more operations of the process 900 may be implemented in the imaging system 100 illustrated in FIG. 1. For example, the process 900 illustrated in FIG. 9 may be stored in the storage 130 in the form of instructions, and invoked and/or executed by the processing engine 120 (e.g., the processor 210 of the computing device 200 as illustrated in FIG. 2, the CPU 340 of the mobile device 300 as illustrated in FIG. 3).

In 910, the determination module 420 may identify a first point of interest (POI) in an image of body contour of a patient. The first POI may correspond to a specific portion of the patient, e.g., the shoulder of the patient, the feet of the patient, the hip of the patient, an elbow of the patient, or the like, or a combination thereof. In some embodiments, the determination module 420 may identify the first POI based on the features of pixel points (e.g., the pixel values) in the image of body contour. For example, if the image of body contour is a gray level image as described in connection with the operation 720, the determination module 420 may designate the pixel point having the maximum gray value as the first POI in the image of body contour. As described elsewhere in the disclosure, the pixel point having the maximum gray value may correspond to the largest pressure value on a corresponding pressure sensor. Assuming that the shoulder of the patient imposes the largest pressure on the scanning board, the first POI in the image of body contour may correspond to a pressure sensor under the shoulder of the patient. In some embodiments, the determination module 420 may identify the first POI in the image of body contour according to a marker installed on the scanning board or a specific portion of the patient (e.g., the shoulder of the patient). For example, the first POI may represent the marker presented in the image of body contour.

In 920, the determination module 420 may identify a second POI in a structure image of the patient as described in connection with the operation 830. The second POI in the structure image of the patient and the first POI in the image of body contour of the patient may correspond to a same location. For example, both of the first POI and the second POI may correspond to the shoulder of the patient. As another example, the first POI may represent a marker presented in the image of body contour and the second POI may represent the same marker presented in the structure image.

In 930, the image generation module 440 may combine the image of body contour and the structure image. As the first POI and the second POI correspond to a same portion of the patient, the image generation module 440 may merge the organs presented in the structure image with the body contour of the patient in the image of body contour. And thus, the combined image may include the position information of the organs with respect to the scanning board as described elsewhere in the disclosure.

In 940, the determination module 420 may determine the position of a ROI with respect to a scanning board based on the combined image of the patient. The ROI may include at least one of the organs of the patient. More description regarding the determination of the position of the ROI may be found elsewhere in the disclosure (e.g., in connection with the operations 520 and 630, and the descriptions thereof).

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. In some embodiments, one or more operations may be added or omitted. For example, the operation 930 may be omitted. Thus, the position of the ROI with respect to the scanning board may be determined based on the first POI and the second POI without combining the image of body contour and the structure image of the patient.

FIG. 10 is a flowchart illustrating an exemplary process 1000 for determining the position of a ROI with respect to an imaging device according to some embodiments of the present disclosure. The operation 520 as illustrated in FIG. 5 may be performed according to the process 1000. In some embodiments, one or more operations of the process 1000 may be implemented in the imaging system 100 illustrated in FIG. 1. For example, the process 1000 illustrated in FIG. 10 may be stored in the storage 130 in the form of instructions, and invoked and/or executed by the processing engine 120 (e.g., the processor 210 of the computing device 200 as illustrated in FIG. 2, the CPU 340 of the mobile device 300 as illustrated in FIG. 3).

In 1010, the image generation module 440 may generate an image of a patient disposed on a scanning board of an imaging device. The image may include position information of a reference object with respect to the imaging device and information associated with one or more organs of the patient. The reference object may include a marker that is disposed outside the patient and installed on the scanning board of the imaging device. In some embodiments, the image of the patient may be generated by a thermal imaging device that is capable of imaging the one or more organs of the patient and the marker simultaneously.

In 1020, the determination module 420 may determine the position of a ROI with respect to the imaging device based on the position information of the reference object with respect to the imaging device. As described elsewhere in the disclosure, the ROI may include at least one of the one or more organs of the patient. According to the position information of the reference object with respect to the image device (e.g., the position of the reference object on the scanning board) and the spatial correlation between the reference object and the one or more organs of the patient presented in the image, the determination module 420 may determine the position of the first ROI with respect to the imaging device. For example, a marker may be located at a first position (referred to as "$\vec{L}_A$") on the scanning board. As used herein, $\vec{L}_A$ may denotes a coordinate with respect to the origin of a coordinate system of the imaging system 100. The relative positions between the marker and the ROI (e.g., the heart region of the subject) presented in the image may be expressed as "$\vec{L}_{AtoR}$", and thus the position of the ROI with respect to the scanning board may be expressed as:

$$\vec{L}_R = \vec{L}_A + \alpha \cdot \vec{L}_{AtoR} \qquad (1)$$

where $\vec{L}_R$ denotes the position of the ROI with respect to the scanning board, and a denotes an image scale that indicates the relationship between the size of a specific object presented in the image and the actual size of the specific object.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

Figure 11:
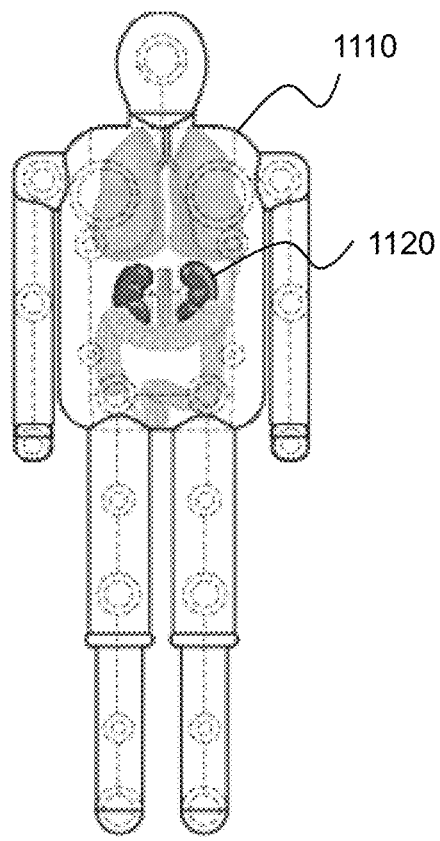
FIG. 11 is a schematic diagram illustrating an image of a patient according to some embodiments of the present disclosure.

FIG. 11 is a schematic diagram illustrating an image of a patient according to some embodiments of the present disclosure. The image of the subject may include a body contour 1010 and a ROI 1020 of the patient. As shown, the ROI 1020 includes the liver of the patient which is enclosed in the body contour 1010.

Figure 12:
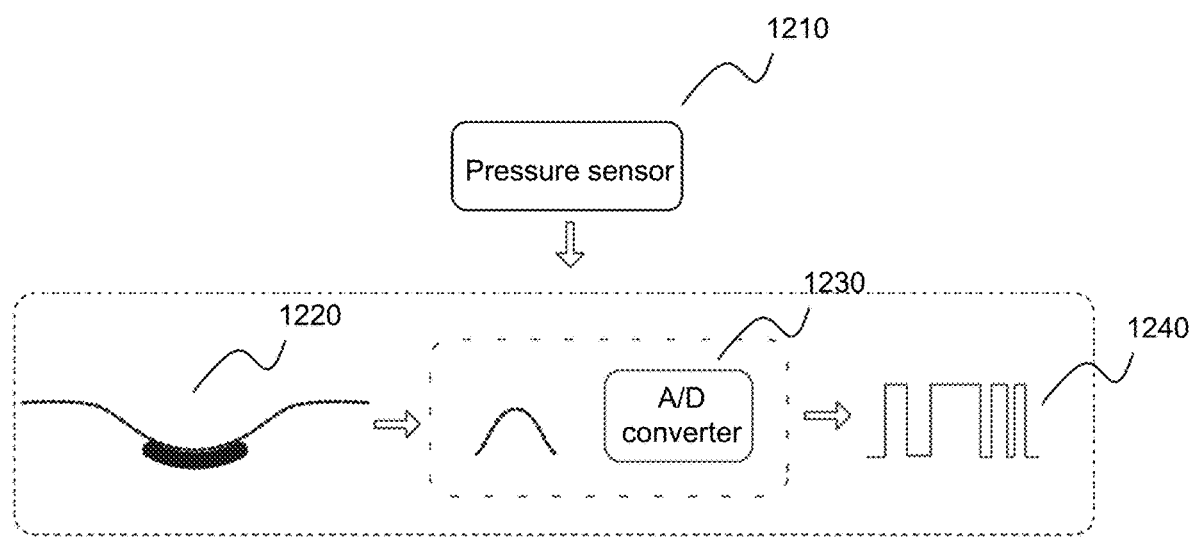
FIG. 12 is a schematic diagram illustrating an exemplary process for acquiring measurements from a pressure sensor according to some embodiments of the present disclosure.

FIG. 12 is a schematic diagram illustrating an exemplary process for acquiring measurements from a pressure sensor according to some embodiments of the present disclosure. As shown, the pressure sensor 1210 may include a pressure detector 1220 and an A/D converter 1230. The pressure detector 1220 may detect a pressure and convert the pressure into an analog signal (e.g., a voltage analog signal). The A/D converter 1230 may convert the analog signal to a digital signal 1240. And then, an image may be generated according to the digital signal 1240.

FIG. 13 is a schematic diagram illustrating a pressure sensor network arranged on a scanning board according to some embodiments of the present disclosure. The pressure sensor network 1310 may include a plurality of pressure sensors arranged on a scanning bed 1320. As shown, the pressure sensor network 1310 is presented in the form of a 2D matrix, where each dot represents a pressure sensor. The pressure sensor network 1310 may include a plurality of rows and columns. The interval between two adjacent rows in the pressure sensor network 1310 is represented by a, which can be any suitable values, e.g., 0.5 cm, 1.0 cm, 2.0 cm, or the like. The interval between two adjacent columns in the pressure sensor network 1310 is represented by d, which can be any suitable values, e.g., 0.5 cm, 1.0 cm, 2.0 cm, or the like. In some embodiments, the interval between two adjacent columns may be equal to the interval between two adjacent rows (i.e., a is equal to d).

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and describe.

We claim:

1. A system comprising: a non-transitory computer-readable storage medium storing executable instructions, and at least one processor in communication with the computer-readable storage medium, when executing the executable instructions, causing the system to implement a method, comprising: generating a first image of a subject disposed on a scanning board of an imaging device, the first image including position information of the subject, wherein the first image is generated based on information collected by a plurality of pressure sensors arranged on the scanning board; generating a second image of the subject, the second image including information associated with one or more organs of the subject; determining, based on the first image and the second image, a position of a region of interest (ROI), the ROI including at least one of the one or more organs of the subject; and operating the imaging device to scan a target portion of the subject including the ROI of the subject.

2. The system of claim 1, wherein the generating a first image of the subject comprises:
receiving, from the plurality of pressure sensors disposed on the scanning board, a plurality of measurements associated with pressure generated by the subject;
generating a body contour of the subject based on the plurality of measurements associated with pressure generated by the subject; and
generating the first image of the subject based on the body contour of the subject.

3. The system of claim 2, wherein the plurality of measurements indicate a plurality of pressure values obtained by the plurality of pressure sensors, respectively.

4. The system of claim 1, wherein the generating a second image of the subject comprises:
receiving information associated with thermal distribution of the subject; and
generating the second image of the subject using thermal tomography based on the thermal distribution.

5. The system of claim 1, wherein the generating a second image of the subject comprises:
acquiring physiological data related to the subject; and
generating, based on the physiological data and anatomical information associated with organs of the subject, the second image of the subject.

6. The system of claim 1, wherein the determining, based on the first image and the second image, a position of a region of interest (ROI) comprises:
generating a third image of the subject by combining the first image and the second image; and
determining, based on the third image of the subject, the position of the ROI.

7. The system of claim 6, wherein the generating a third image of the subject by combining the first image and the second image comprises:
identifying a first point of interest (POI) in the first image of the subject;
identifying a second POI in the second image of the subject, the second POI and the first POI corresponding to a same physical location; and
combining; based on the first POI and the second POI, the first image and the second image.

8. The system of claim 1, wherein the determining, based on the first image and the second image, a position of a region of interest (ROI) comprises:
identifying a third POI in the first image of the subject;
identifying a fourth POI in the second image of the subject, the third POI and the fourth POI corresponding to a same physical location; and
determining, based on the third POI and the fourth POI, the position of the ROI.

9. The system of claim 1, wherein the operating the imaging device to scan a target portion of the subject including the ROI of the subject comprises:
determining at least one boundary line to delimit the target portion; and
operating the imaging device to scan the subject according to the at least one boundary line.

10. A method implemented on a computing device having at least one processor, at least one non-transitory computer-readable storage medium, and a communication port connected to an imaging device, the method comprising:
generating a first image of a subject disposed on a scanning board of the imaging device, the first image including position information of the subject with respect to the imaging device, wherein the first image is generated based on information collected by a plurality of pressure sensors arranged on the scanning board; generating a second image of the subject, the second image including information associated with one or more organs of the subject; determining, based on the first image and the second image, a position of a region of interest (ROI) with respect to the imaging device, the ROI including at least one of the one or more organs of the subject; and operating the imaging device to scan a target portion of the subject including the ROI of the subject.

11. The method of claim 10, wherein the generating a first image of the subject comprises:
receiving, from the plurality of pressure sensors disposed on the scanning board, a plurality of measurements associated with pressure generated by the subject;
generating a body contour of the subject based on the plurality of measurements associated with pressure generated by the subject; and
generating the first image of the subject based on the body contour of the subject.

12. The method of claim 11, wherein the plurality of measurements indicate a plurality of pressure values obtained by the plurality of pressure sensors, respectively.

13. The method of claim 10, wherein the generating a second image of the subject comprises:
receiving, information associated with thermal distribution of the subject; and
generating the second image of the subject using thermal tomography based on the thermal distribution.

14. The method of claim 10, wherein the generating a second image of the subject comprises:
acquiring physiological data related to the subject; and
generating, based on the physiological data and anatomical information associated with organs of the subject, the second image of the subject.

15. The method of claim 10, wherein the determining, based on the first image and the second image, a position of a region of interest (ROI) with respect to the imaging device comprises:
generating a third image of the subject by combining the first image and the second image; and
determining, based on the third image of the subject, the position of the ROI with respect to the imaging device.

16. The method of claim 15, wherein the generating a third image of the subject by combining the first image and the second image comprises:
identifying a first point of interest (POI) in the first image of the subject;
identifying a second POI in the second image of the subject, the second POI and the first POI corresponding to a same physical location; and
combining, based on the first POI and the second POI, the first image and the second image.

17. The method of claim 10, wherein the determining, based on the first image and the second image, a position of a region of interest (ROI) with respect to the imaging device comprises:
identifying a third POI in the first image of the subject;
identifying a fourth POI in the second image of the subject, the third POI and the fourth POI corresponding to a same physical location; and
determining, based on the third POI and the fourth POI, the position of the ROI with respect to the imaging device.

18. The method of claim 10, wherein the operating the imaging device to scan a target portion of the subject including the ROI of the subject comprises:
determining at least one boundary line to delimit the target portion; and
operating the imaging device to scan the subject according to the at least one boundary line.

19. A method implemented on a computing device having at least one processor, at least one non-transitory computer-readable storage medium, and a communication port connected to an imaging device, the method comprising: generating an image of the subject disposed on a scanning board of the imaging device, the image including position information of a reference object located outside the subject with respect to the imaging device and information associated with one or more organs of the subject, wherein the image is generated based on information associated with thermal distribution of the subject and the reference object; determining, based on the reference object located outside the subject, a position of a region of interest (ROI) with respect to the imaging device, the ROI including at least one of the one or more organs of the subject; and operating the imaging device to scan a target portion of the subject including the ROI of the subject.

20. The method of claim 19, wherein the reference object is a marker installed on the scanning board.

* * * * *